US00PP37623P2

(12) United States Plant Patent
Farrow

(10) Patent No.: US PP37,623 P2
(45) Date of Patent: Aug. 18, 2026

(54) ***SPIRAEA* PLANT NAMED 'FARROWSJKO'**

(50) Latin Name: *Spiraea japonica*
Varietal Denomination: FARROWSJKO

(71) Applicant: Spring Meadow Nursery Inc, Grand Haven, MI (US)

(72) Inventor: Michael W. Farrow, Warwick, MD (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 19/370,978

(22) Filed: Oct. 28, 2025

(51) Int. Cl.
*A01H 6/74* (2018.01)
*A01H 5/02* (2018.01)

(52) U.S. Cl.
USPC ..... Plt./226

(58) Field of Classification Search
USPC ..... Plt./226
CPC ..... A01H 6/74; A01H 5/02
See application file for complete search history.

*Primary Examiner* — Keith O. Robinson

(57) ABSTRACT

A new and distinct cultivar of *Spiraea* plant named 'FARROWSJKO' is disclosed, characterized by plants that are dense, compact and uniform, with a rounded/mounded overall shape. Reblooming occurs repeatedly with flowering beginning in May or June and continuing until the frost. Flowers are bright pink flowers. Foliage is solid green. The new cultivar is a *Spiraea*, typically produced as an outdoor ornamental plant.

3 Drawing Sheets

Figure 1:
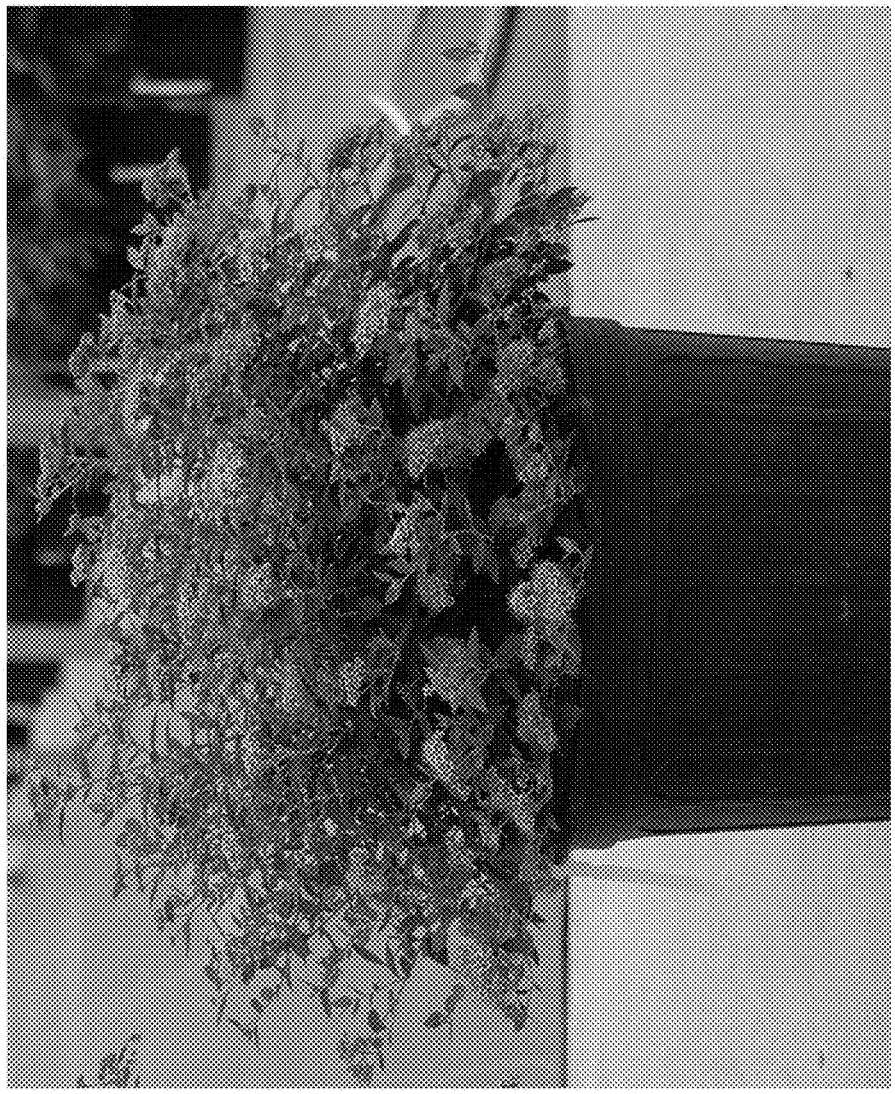

Latin name of the genus and species: *Spiraea japonica*.
Cultivar denomination: 'FARROWSJKO'.

BACKGROUND OF THE INVENTION

The new cultivar is a product of a planned breeding program conducted by the inventor to produce new *Spiraea* cultivars with compact, round habits, high flower coverage, pink flower color. The seed parent is *Spiraea japonica* 'Little Princess', unpatented. The pollen parent is unknown. The open pollination resulting in the new cultivar was made in fall 2014 at a nursery in Warwick, Maryland.

*Spiraea* 'FARROWSJKO' was found and selected at the same nursery in Warwick, Maryland in summer 2015. The first asexual propagation of 'FARROWSJKO' was carried out in summer 2015 by softwood cuttings at the same location in Warwick, Maryland. Through subsequent propagation, multiple additional generations have been reproduced, having shown that the unique features of this cultivar are stable and reproduced true to type.

SUMMARY OF THE INVENTION

The cultivar 'FARROWSJKO' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FARROWSJKO'. These characteristics in combination distinguish 'FARROWSJKO' as a new and distinct *Spiraea* cultivar:

1. Medium green foliage.
2. Dense, compact, uniform habit.
3. Rounded/mounded overall plant shape.
4. Bright pink flower color.

5. High degree of flower coverage.
6. Reblooming/multiple blooming cycles.

PARENTAL COMPARISONS

'FARROWSJKO' is similar to the seed parent in most horticultural characteristics. The new cultivar, however, differs in the following:

1. Plants of the new cultivar have a more dense, compact habit, while plants of the seed parent have a more open habit.
2. Plants of the new cultivar are more well-branched than plants of the seed parent.
3. Flower color of the new cultivar is a more vibrant pink than the flower color of the seed parent.
4. Plants of the new cultivar have more flower coverage than plants of the seed parent.

COMMERCIAL COMPARISON

'FARROWSJKO' can be compared to the commercial cultivar *Spiraea japonica* 'Odessa', U.S. Plant Pat. No. 28,508. The two *Spiraea* are similar in most horticultural characteristics. The new cultivar, however, differs in the following:

1. Leaf shape of the new cultivar is ovate to broadly elliptic, while the leaf shape of this comparator is more elliptic.
2. Young foliage of the new cultivar is entirely green without any reddish-brown tint, while the young foliage of this comparator has a slight reddish-brown tint.

BRIEF DESCRIPTION OF THE PHOTOGRAPHS

This new *Spiraea* is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new hybrid *Spiraea*.

FIG. 1 is a color photograph showing a plant of 'FARROWSJKO' in Grand Haven, Michigan grown in a 3-gallon pot. This plant is about 2 years old.

Figure 2:
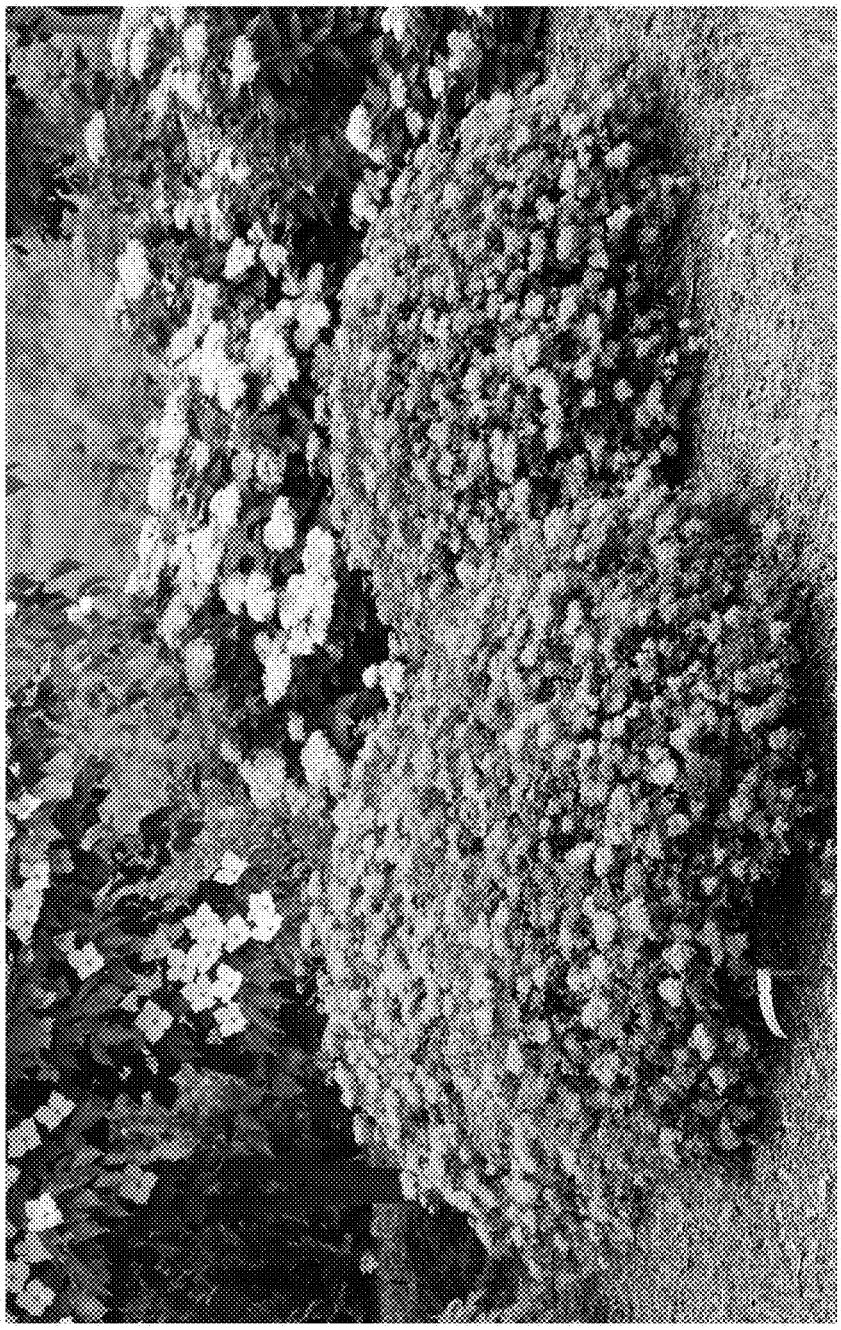

FIG. 2 is a photograph of 3 plants of 'FARROWSJKO' grown outdoors in the ground in Grand Haven, Michigan. Plants are about 5 to 6 years old. The photograph is taken from a side view and shows the plant shape.

Figure 3:
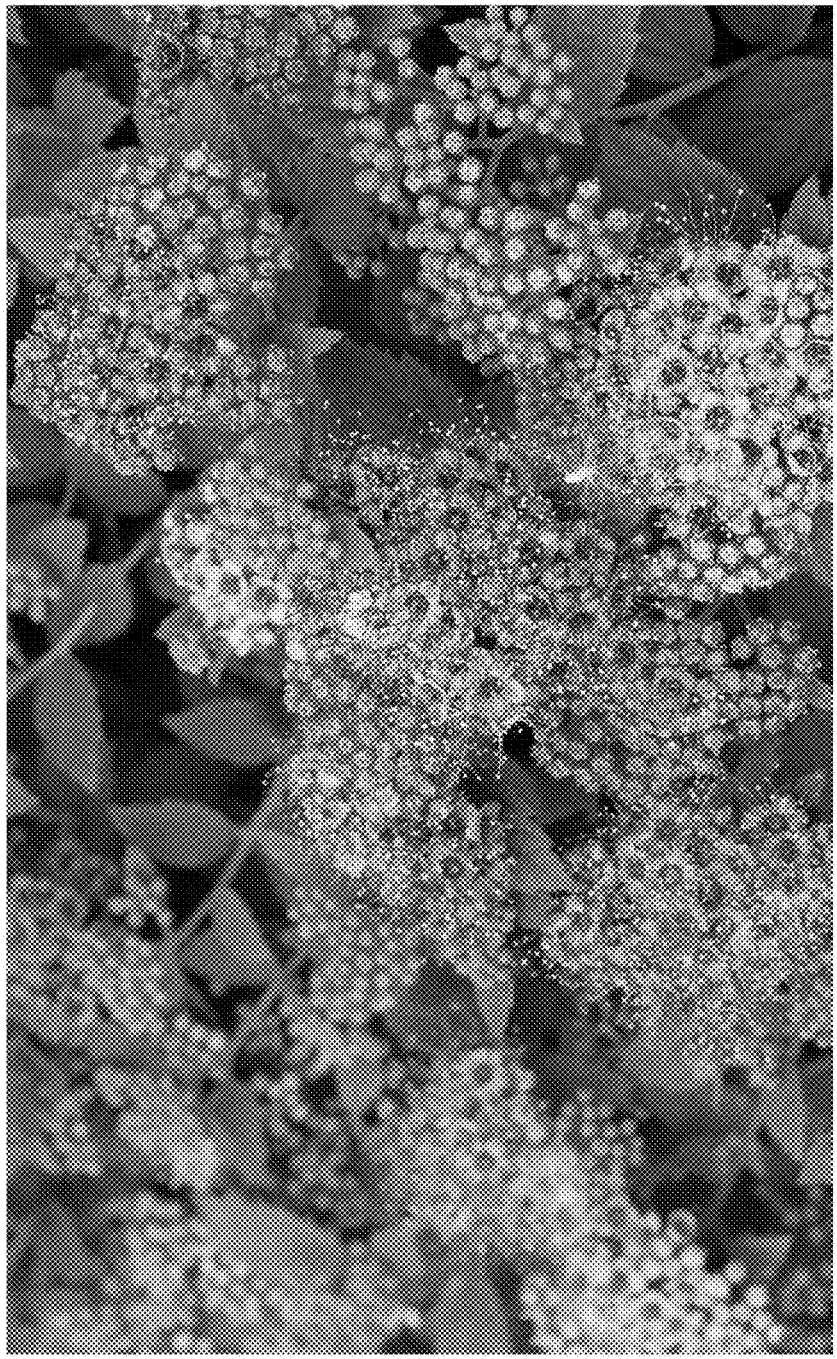

FIG. 3 shows inflorescences and mature foliage of 'FARROWSJKO' in Warwick, Maryland.

DETAILED BOTANICAL DESCRIPTION

In the following description, color references are made to The Royal Horticultural Society Colour Chart 2015, except where general terms of ordinary dictionary significance are used. The following observations and measurements describe 'FARROWSJKO' plants grown in a poly-greenhouse in Grand Haven, Michigan. The plants were 3 years old. Temperatures ranged from 5° C. to 10° C. at night to 18° C. to 27° C. during the day. No artificial light, photoperiodic treatments were given to the plants. Measurements and numerical values represent averages of typical plant types.

Botanical classification: *Spiraea japonica* 'FARROWSJKO'.

PROPAGATION

Typical method: Softwood cuttings.

Root initiation: 21 days in summer at approximately 25° C.

Time to produce rooted cutting: About 60 days in summer at approximately 25° C.

Roots: Dense, freely branching, medium thickness, fibrous. White in color, not accurately measured with R.H.S. chart.

PLANT

Plant type: Perennial shrub.

Growth habit: Compact, rounded/mounded.

Shape: Globose.

Height: 40 cm.

Plant spread: 55 cm.

Pot size of plant described: 5 gallon.

Age of plant described: 3 years.

Growth rate: 14 weeks to produce a finished 1-quart pot from a cutting.

Stem:

- *Branching*.—Freely.
- *Pinching*.—Some required to encourage well-rounded habit.
- *Number of lateral branches*.—Around 100.
- *Shape*.—Rounded.
- *Color*.—Immature: RHS Yellow-Green 144D. Mature: RHS Greyed-Orange 165A.
- *Length*.—35 cm.
- *Width*.—2 mm.
- *Aspect*.—0° to 45° from vertical.
- *Strength*.—Medium.
- *Pubescence*.—Slight on new growth only.
- *Internode length*.—1 cm.

FOLIAGE

Leaf:

- *Arrangement*.—Alternate, single.
- *Shape*.—Ovate to broadly elliptic.
- *Length*.—2 cm.
- *Width*.—1 cm.
- *Apex*.—Acute.
- *Base*.—Cuneate.
- *Margin*.—Serrate.
- *Quantity per plant*.—About 3000.
- *Aspect*.—Mainly flat with very slight downward curve.
- *Texture of top surface*.—Glabrous.
- *Texture of bottom surface*.—Glabrous with raised venation.
- *Pubescence*.—None.
- *Fragrance*.—None.
- *Color*.—Young Foliage, Upper Side: RHS Green 137B. Young Foliage, Under Side: RHS Green 137C. Mature Foliage, Upper Side: RHS Green 137B. Mature Foliage, Under Side: RHS Green 137C.

Venation:

- *Type*.—Palmate.
- *Color*.—Mature, Upper Side: RHS Green 137C. Mature, Under Side: RHS Green 137C.

Petiole:

- *Length*.—1 mm.
- *Width*.—1 mm.
- *Strength*.—Strong.
- *Color*.—Upper Side: RHS Yellow-Green 144D. Under Side: RHS Yellow-Green 144D.
- *Texture*.—Upper Side: Glabrous. Under Side: Glabrous.

INFLORESCENCE

Natural flowering season: First bloom in summer (May, June) with repeat blooming until frost.

Flower arrangement: Freely flowering with terminal inflorescences.

Flowering habit: Terminal.

Compound corymb. 26 Inflorescence Type:

Height: 3 cm.

Diameter: 4 cm.

Quantity of flowers per inflorescence: About 60.

Quantity of flowers per lateral stem: About 60.

Quantity of buds per lateral stem: About 90.

Quantity of flowers and buds per plant: About 10,000.

Fragrance: Mild, slightly sweet.

Flower:

- *Type or form*.—Rotate, single whorl.
- *Aspect*.—Upright.
- *Length*.—7 mm.
- *Diameter*.—7 mm.
- *Depth*.—5 mm.
- *Persistence*.—Persistent.
- *Longevity*.—About 2 weeks.

Bud:

- *Length*.—1 mm.
- *Diameter*.—2 mm.
- *Shape*.—Globose.
- *Color*.—RHS Red-Purple 64B.

Petals:
*Number.*—5.
*Arrangement.*—Stellate, single rotate.
*Shape.*—Broadly ovate to globose.
*Tip.*—Obtuse.
*Base.*—Obtuse.
*Margin.*—Entire.
*Length.*—3 mm.
*Width.*—3 mm.
*Texture.*—Upper side: Glabrous, silky. Under side: Glabrous, silky.
*Color.*—When Opening, Upper Side: RHS Red-Purple 64B. When Opening, Under Side: RHS Red-Purple 63C. Fully Opened, Upper Side: RHS Red-Purple 64B with areas of Red-Purple 64D at the margins. Fully Opened, Under Side: RHS Red-Purple 63C. Fading, Upper Side: RHS Red-Purple 65B. Fading, Under Side: RHS Red-Purple 65B.

Sepals:
*Number.*—5.
*Arrangement.*—Whorl; inconspicuous.
*Shape.*—Triangular.
*Tip.*—Acute.
*Base.*—Fused.
*Margin.*—Entire.
*Length.*—1 mm.
*Width.*—1 mm.
*Texture.*—Upper side: Glabrous. Under side: Glabrous.
*Color.*—Mature, Upper Side: RHS Green NN137A. Mature, Under Side: RHS Green NN137A.

Calyx:
*Shape.*—Collar-like.
*Length.*—4 mm.
*Diameter.*—4 mm.

Peduncle:
*Terminal length.*—2 cm.
*Terminal diameter.*—1 mm.
*Angle.*—0° from vertical (in line with lateral branch).
*Strength.*—Moderate to high.
*Texture.*—Glabrous.
*Color.*—RHS Yellow-Green 146A.

Pedicel:
*Length.*—5 mm.
*Diameter.*—1 mm.
*Angle.*—45° relative to peduncle.
*Strength.*—Moderate.
*Texture.*—Glabrous.
*Color.*—RHS Yellow-Green 146A.

REPRODUCTIVE ORGANS

Stamens:
*Number.*—About 20.
*Filament length.*—5 mm.
*Filament color.*—RHS Red-Purple 64B.

Anthers:
*Shape.*—Globose.
*Length.*—1 mm.
*Color.*—RHS Red-Purple 64B.
*Pollen amount.*—Low.
*Pollen color.*—RHS Yellow 2D.

Pistil:
*Number.*—5.
*Length.*—2 mm.

Stigma:
*Shape.*—Rounded.
*Color.*—RHS Red 39D.
*Style length.*—1.5 mm.
*Style color.*—RHS Red 39D.
*Ovary color.*—RHS Yellow-Orange 16C to 16D.

OTHER CHARACTERISTICS

Fruit and seed: Not observed.
Disease and insect resistance: Resistant to powdery mildew (Various species of *Podosphaera*).
Temperature tolerance: Hardy in USDA Zones 3 to 8.

What is claimed is:

1. A new and distinct cultivar of *Spiraea* plant named 'FARROWSJKO' as herein illustrated and described.

* * * * *